US009820996B2

(12) United States Patent
Chen

(10) Patent No.: US 9,820,996 B2
(45) Date of Patent: Nov. 21, 2017

(54) PREPARATION METHOD FOR ANTITHYROID OINTMENT FOR EXTERNAL APPLICATION

(71) Applicant: Ling Chen, Shandong Province (CN)

(72) Inventor: Ling Chen, Shandong Province (CN)

( * ) Notice: Subject to any disclaimer, the term of this patent is extended or adjusted under 35 U.S.C. 154(b) by 0 days.

(21) Appl. No.: 15/325,444

(22) PCT Filed: Jul. 16, 2015

(86) PCT No.: PCT/CN2015/000509
§ 371 (c)(1),
(2) Date: Jan. 11, 2017

(87) PCT Pub. No.: WO2016/008283
PCT Pub. Date: Jan. 21, 2016

(65) Prior Publication Data
US 2017/0157144 A1    Jun. 8, 2017

(30) Foreign Application Priority Data
Jul. 16, 2014  (CN) .......................... 2014 1 0338179

(51) Int. Cl.
A61K 9/14        (2006.01)
A61K 38/22       (2006.01)
A61K 38/29       (2006.01)
A61K 31/573      (2006.01)
A61K 31/4164     (2006.01)
A61K 31/4172     (2006.01)
A61K 31/513      (2006.01)
A61K 31/56       (2006.01)
A61K 47/44       (2017.01)
A61K 47/10       (2017.01)
A61K 47/34       (2017.01)
A61K 47/14       (2017.01)
A61K 47/22       (2006.01)
A61K 47/20       (2006.01)
A61K 47/30       (2006.01)
A61K 9/06        (2006.01)

(52) U.S. Cl.
CPC .............. *A61K 31/573* (2013.01); *A61K 9/06* (2013.01); *A61K 31/4164* (2013.01); *A61K 31/4172* (2013.01); *A61K 31/513* (2013.01); *A61K 31/56* (2013.01); *A61K 47/10* (2013.01); *A61K 47/14* (2013.01); *A61K 47/20* (2013.01); *A61K 47/22* (2013.01); *A61K 47/30* (2013.01); *A61K 47/34* (2013.01); *A61K 47/44* (2013.01)

(58) Field of Classification Search
None
See application file for complete search history.

(56) References Cited

FOREIGN PATENT DOCUMENTS

| CN | 1085079   | 4/1994  |
|----|-----------|---------|
| CN | 1692940   | 11/2005 |
| CN | 101134108 | 3/2008  |
| CN | 101426479 | 5/2009  |
| CN | 102309756 | 1/2012  |
| CN | 104117066 | 10/2014 |

OTHER PUBLICATIONS

Yang et al.; Saudi J of Ophthalmology; (2011) 25(3); pp. 3-13.*
Machine translation for IDS reference CN1084078A provided Aug. 4, 2017.*
Machine translation for IDS reference CN1085079A provided Aug. 4, 2017.*
Machine translation for IDS reference CN1692940A provided Aug. 4, 2017.*
"International Search Report (Form PCT/ISA/210)", dated Oct. 26, 2015, with English translation thereof, pp. 1-4.

* cited by examiner

Primary Examiner — Jeffrey T. Palenik
(74) Attorney, Agent, or Firm — JCIPRNET

(57) ABSTRACT

A preparation method for an antithyroid ointment for external application is provided. The ointment includes the following components by mass percentage: 0.01-10% gluco corticoid, 1-15% antithyroid drug, 0.1-30% percutaneous penetration enhancer, 10-30% oleaginous base and 4-40% water-soluble base. The method includes: mixing the glucocorticoid and a drug carrier material so as to evenly disperse the glucocorticoids on the drug carrier material to obtain a glucocorticoid component; placing and evenly mixing an antithyroid drug and other ingredients in distilled water, and heating to 80° C. and evenly mixing to obtain a water phase; melting an oleaginous base and a percutaneous penetration enhancer at 80° C. and evenly mixing to obtain an oil phase; maintaining at 80° C. and pouring the oil phase into the water phase, and evenly stirring; adding the glucocorticoid component when the temperature drops to 40° C.; and evenly and sufficiently stirring until cooled to obtain an ointment.

5 Claims, No Drawings

PREPARATION METHOD FOR ANTITHYROID OINTMENT FOR EXTERNAL APPLICATION

CROSS-REFERENCE TO RELATED APPLICATION

This application is a 371 application of the International PCT application serial no. PCT/CN2015/000509, filed on Jul. 16, 2015, which claims the priority benefit of China application no. 201410338179.1, filed on Jul. 16, 2014. The entirety of each of the above-mentioned patent applications is hereby incorporated by reference herein and made a part of this specification.

BACKGROUND OF THE INVENTION

Field of the Invention

The invention relates to a field of antithyroid ointment drugs for external application, and more particularly to a preparation method for an antithyroid ointment for external application.

Description of Related Art

Hyperthyroidism is a common disease, and in the last seventy years, oral imidazole and thiourea antithyroid drugs (oral antithyroid drugs in the following context) have been the first choice and main treatment method for hyperthyroidism. The method is slower in controlling hyperthyroidism, the efficacy is not stable enough, some systemic adverse reactions may be produced, and the remission rate is lower after drug use is discontinued. Therefore, in 1993, Ling Chen, et, al., developed and applied for the invention patent "Antithyroid cream for external application" and have been granted a patent, with the patent number ZL93111370.9. The patent disclosed an oil-in-water cream containing an anti-thyroid drug and glucocorticoids, and the application of the cream on skin on the thyroid to treat hyperthyroidism produced better effects than oral antithyroid drugs, and no significant systemic side effects were observed. In clinical applications, it was found that significant adverse skin reactions occurred on the application site on the neck of many hyperthyroidism patients using the antithyroid cream for external application, and therefore the application of the drug was significantly limited.

Therefore, Ling Chen further applied for the invention patent "External-applied ointment used for treating thyropathy, and its preparing method" in 2005, which was also granted a patent, with the patent number is ZL200510070954.0. The patent disclosed an oil-in-water cream containing an antithyroid drug, glucocorticoids, a percutaneous penetration enhancer, an oleaginous base, a water-soluble base, a preservative, and an antioxidant as raw materials. This agent produced less local skin adverse reactions than the agent of patent 1, but preclinical studies showed that, the stability of glucocorticoids, one of the main drugs, was poor, and the efficacy and shelf life of the agent were affected. Moreover, it was found from more clinical applications for more patients and a longer period that, a greater occurrence of local skin adverse reaction still existed, which affects the compliance of patients to treatment.

SUMMARY OF THE INVENTION

An object of the invention is to overcome the drawbacks of existing drugs and provide a preparation method for an antithyroid ointment for external application such that the antithyroid ointment agent for external application has good stability, less local skin adverse reaction, better efficacy, and no significant systemic side effects.

The technical solution of the invention is implemented as follows. The invention discloses a preparation method for an antithyroid ointment for external application, including the steps of:

(1) mixing glucocorticoids and a drug carrier material so as to evenly disperse the glucocorticoids on the drug carrier material to obtain a glucocorticoid component;

(2) placing and evenly mixing an antithyroid drug, a water-soluble base, a preservative, an antioxidant, and an emulsifier in distilled water, and then heating to 80° C. and evenly mixing again to obtain a water phase;

(3) melting an oleaginous base and a percutaneous penetration enhancer at 80° C., and evenly mixing to obtain an oil phase;

(4) maintaining at 80° C. and pouring the oil phase obtained in step (3) into the water phase obtained in step (2) and evenly stirring, and adding the glucocorticoid component prepared in step (1) when the temperature drops to 40 t to obtain a mixture; and (5) evenly and sufficiently stirring the mixture obtained in step (4) again until cooled to obtain an ointment;

wherein in the ointment, the mass percentage of the glucocorticoids is 0.01% to 10%, the mass percentage of the antithyroid drug is 1% to 15%, the mass percentage of the percutaneous penetration enhancer is 0.1% to 30%, the mass percentage of the oleaginous base is 10% to 30%, and the mass percentage of the water-soluble base is 4% to 40%.

In the preparation method of the invention, the preparation of step (1) adopts any method below:

mixing the glucocorticoids and the drug carrier material to form a solid dispersion by a melting method, a solvent method, or a mechanical dispersion method, wherein the drug carrier material is any one of polyethylene glycol 1000 to polyethylene glycol 10000, povidone, poloxamer 188, polyoxyethylene, carboxypropyl cellulose, and carboxymethyl cellulose;

adding the glucocorticoids to polyethylene glycol 400, and then grinding them into a uniform suspension;

mixing the glucocorticoids and cyclodextrin and a derivative thereof to form an inclusion compound by a saturated aqueous solution method, a grinding method, an ultrasonic method, a freeze-drying method, or a spray drying method;

mixing the glucocorticoids and a phospholipids to form a complex by an evaporation method, a vacuum drying method, a freeze-drying method, or a non-solvent precipitation method; and preparing the glucocorticoids in a colloidal dispersion system, wherein the colloidal dispersion system includes any one of solid lipid nanoparticles (SLN), nanostructured lipid carriers (NLC), and polymeric micelles.

In the preparation method of the invention, the glucocorticoids includes any one of fluocinolone and acetate thereof; triamcinolone, acetate thereof, isobutyrate thereof and succinate thereof; halcinonide; hydrocortisone, acetate thereof, butyrate thereof, butyrate propionate thereof, cipionate thereof, tertiary butyl acetate thereof valerate thereof and aceponate thereof; dexamethasone, acetate thereof, diisopropyl fluoro phosphate ester thereof, metasulfobenzoate thereof, tert-butylacetate thereof 2-chloro-62-fluoro ester thereof (halometasone), trioxo-undecanoate thereof, isonicotinate thereof and valerate thereof fludrocortisone, acetate thereof and succinate thereof triamcinolone acetonide and acetate thereof betamethasone, acetate thereof, dipropionate thereof, acibutate thereof, valerate thereof, succinate thereof, benzoate thereof, phosphate thereof and valeroacetate thereof; beclomethasone and dipropionate thereof; clobetasol propionate; flurandrenolide; prednisone, acetate thereof and palmitate thereof; prednisolone, acetate thereof, metasulfobenzoate thereof, palmitate thereof, valerate thereof and valeroacetate thereof; diflorasone and acetate thereof; amcinonide; mometasone and furoate thereof; methylprednisolon, acetate thereof, cipionate thereof, phosphate thereof and succinate thereof; clobetasone butyrate, fluorometholone; alclometasone and dipropionate thereof; difluprednate; deprodone and propionate thereof; fludroxycortide; and desoximetasone.

In the preparation method of the invention, the antithyroid drug includes any one of an imidazole antithyroid drug and a thiourea antithyroid drug, wherein the imidazole antithyroid drug is methimazole or carbimazole, and the thiourea antithyroid drug is propylthiouracil or methylthiouracil.

In the preparation method of the invention, the oleaginous base includes any three or more of vaseline, stearic acid, glyceryl monostearate, white wax, beeswax, cetyl alcohol, stearyl alcohol, dimethyl polysiloxane, toluene polysilicon, ethylene glycol monostearate, lauric acid, and silicon oil.

In the preparation method of the invention, the water-soluble base includes any one or more of polyethylene glycol 200 to polyethylene glycol 600, isopropyl myristate, sodium alginate, methyl cellulose, hydroxymethyl cellulose, carboxyethyl cellulose, glycerol gelatin, and glycerin of starch.

In the preparation method of the invention, the percutaneous penetration enhancer includes any one or two of azone, 1-geranyl-azepan-2-one, 1-farnesyl-azepan-2-one, 2-pyrrolidone, 1-methyl-2-pyrrolidone, 5-methyl-2-pyrrolidone, 1,5-dimethyl-2-pyrrolidone, 1-ethyl-2-pyrrolidone, 2-pyrrole-5-carboxylic acid, dimethyl sulfoxide, dodecyl methyl sulfoxide, decyl methyl sulfoxide, hexamethylene lauramide, urea, and oleic acid.

In the preparation method of the invention, the emulsifier includes any one or two of sodium dodecyl sulfate (SDS), poloxamer 188, Tweens, Spans, Brijs, cetomacrogol 1000 (CMG), peregals, fatty alcohol polyoxyethylene ether (AEO), and alkylphenol ethoxylates (Igepon, APE).

In the preparation method of the invention, the preservative includes any one or more of methylparaben, ethylparaben, propylparaben, butylparaben, sorbic acid, potassium sorbate, calcium sorbate, and benzyl alcohol thymol.

In the preparation method of the invention, the antioxidant includes any one or more of sodium sulfite, sodium bisulfate, sodium metabisulfite, sodium thiosulfate, cysteine, thioglycerol, thioglycol, dithioglycerol, dithiooxamide, thiosorbic acid, thioglucose, isoascorbic acid, and di-tert-butyl-p-cresol.

In the preparation method of the invention, preferably: in the ointment, a mass percentage of the glucocorticoids is 0.02% to 1%, a mass percentage of the antithyroid drug is 3% to 10%, a mass percentage of the percutaneous penetration enhancer is 5% to 20%; a mass percentage of the oleaginous base is 12% to 25%, and a mass percentage of the water-soluble base is 10% to 30%.

In the preparation method of the invention, preferably: in the ointment, a mass percentage of the isopropyl myristate is 6%, a mass percentage of the stearic acid is 6%, a mass percentage of the glyceryl monostearate is 6%, and a mass percentage of the vaseline is 4%.

The effects of the invention are described herein:

1. The preparation method of the invention includes adding glucocorticoids in a drug carrier material to form a solid dispersion, inclusion compound, or complex, or form solid lipid nanoparticles, nanostructured lipid carriers, or polymer micelles of glucocorticoids, such that the stability and solubility of the drug are increased, and the drug quality, efficacy, and validity are ensured and improved. In the conventional preparation method, since the chemical stability and solubility of glucocorticoids in the oil-in-water ointment are poor, glucocorticoids do not readily pass through the skin to reach the lesion site, and therefore the transdermal absorption and efficacy of the drug are affected. In the ointment prepared by the preparation method of the invention, glucocorticoids are first made into a dispersion, such that glucocorticoids are evenly dispersed on the drug carrier material, and as a result the solubility and stability thereof are increased, and the drug quality, efficacy, and validity are ensured and improved.

2. The glucocorticoid composition prepared by the above method is mixed with an oil-in-water ointment at a lower temperature, which further increases the stability of the glucocorticoids. In the preparation method of the invention, the temperature of the oil-in-water ointment reduces to 40° C. from 80° C., and then the glucocorticoid composition is added such that the glucocorticoids are not readily hydrolyzed and oxidized, and the mass stability thereof is increased.

3. In the ointment prepared by the preparation method of the invention, glucocorticoids are more evenly dispersed in the oil-in-water ointment, and as a result, after the ointment is applied on the skin, glucocorticoids are in contact with the skin in a more rapid and better way, such that the transdermal absorption effect of the drug is significantly increased, and the treatment effect of the drug is increased.

4. In addition to polyethylene glycol, other auxiliary components of the invention are also adjusted. These adjustments may seem to be easier, but are actually very difficult for an agent that is applied to the neck long-term on a frequent basis and requiring very high local safety. In the invention, components irritating or allergic to the skin and significantly affecting normal skin function are removed. For instance, carbomer, lanolin, and liquid paraffin in the patent (ZL200510070954.0) are removed; isopropyl myristate is added, a suitable mass of a solid oleaginous base (vaseline, stearic acid, or glyceryl monostearate) is selected, such that adverse skin reactions are reduced. In the invention, an emulsifier is added, and a more suitable type and mass are selected, such that the agent is more stable and the percutaneous absorption of the main drug is better.

5. Stability tests showed that the agent of the invention is stable. Inspection is performed using a sample retention observation method and an accelerated test method, and the results showed that the physical and chemical properties of the agent of the invention are stable, and at room temperature, the drug is valid for 2 years; and the validity of the agent of the patent (ZL200510070954.0) is shorter.

6. In vitro transdermal absorption tests showed that, the cumulative transdermal capacity of the antithyroid drug and the glucocorticoids of the agent of the invention is significantly higher than that of the agent of the patent (ZL200510070954.01 ($P<0.05$). Animal pharmacokinetics showed that, comparing local skin administration and oral administration of the agent of the invention, the content of the two drugs locally administered is significantly increased in the thyroid ($P<0.01$), and the concentration in blood is not significantly increased ($P>0.05$).

7. Clinical trials showed that, the cream of the invention produced no significant systemic side effects and further reduced the main drawbacks of the patent (ZL200510070954.0), i.e., the adverse skin reaction at the application site on the neck, and patient discomfort is significantly reduced and compliance of patient drug use is increased; at the same time, the effect of the treatment for hyperthyroidism is increased, and a stable therapeutic drug that is safer and has better efficacy is thus provided for hyperthyroidism patients, and therefore the invention is suitable for large-scale promotion and application.

DESCRIPTION OF THE EMBODIMENTS

The features of the invention are further described via specific examples herein.

The raw material components and mass percentage contents of examples 1 to 7 are provided in Table 1.

(3) melting an oleaginous base and a percutaneous penetration enhancer at 80° C. and mixing the two evenly to obtain an oil phase;

(4) pouring the oil phase obtained in step (3) into the water phase obtained in step (2), heating the mixture to 80° C., and stirring the mixture evenly;

(5) adding the prednisolone-povidone solid dispersion powder prepared in step (1) when the temperature was reduced to 40° C.;

(6) stirring the mixture evenly and sufficiently again until cooled to obtain an ointment.

TABLE 1

| Component content (mass %) | Example 1 | 2 | 3 | 4 | 5 | 6 | 7 |
|---|---|---|---|---|---|---|---|
| Prednisolone-povidone | 0.5-5 | | | | | | |
| Fluocinolone-β-cyclodextrin | | 0.025-0.5 | | | | | |
| Hydrocortisone-polyethylene glycol | | | 1-10 | 0.5-5 | | | |
| Mometasone-soybean phospholipids | | | | | 0.1-2 | | |
| Butyric acid hydrocortisone-poloxamer 188 | | | | | | 0.1-2 | |
| Halometasone-solid lipid nanoparticles | | | | | | | 0.05-1 |
| Propylthiouracil | | | 10 | | | | 8 |
| Methimazole | 6 | 5 | | 7 | 4 | 3 | |
| Azone | 2 | 5 | 6 | 3 | 4 | | |
| Isopropyl myristate | 7 | 4 | 3 | 6 | 4 | 5 | 6 |
| 1-methyl-2-pyrrolidone | | | | | | 2 | 1 |
| Glyceryl monostearate | 2 | 8 | 7 | 6 | 5 | 4 | 3 |
| Stearic acid | 9 | 2 | 3 | 4 | 6 | 7 | 8 |
| Vaseline | 3 | 5 | 6 | 4 | 7 | 2 | 1 |
| Sorbic acid | 0.1 | 0.05 | 0.05 | | | | 0.2 |
| Ethylparaben | | 0.15 | | 0.1 | 0.05 | 0.2 | |
| Propylparaben | 0.2 | | 0.1 | | 0.05 | | |
| Sodium sulfite | 0.2 | 0.3 | | 0.1 | 0.4 | | |
| Sodium bisulfite | | | 0.1 | | | 0.15 | 0.2 |
| Sodium dodecyl sulfate | 0.3 | 0.2 | 0.4 | 0.1 | | | |
| Tween | | | | | 5 | 2 | 3 |
| Span | | | | | | 1 | 2 |
| Water | Margin | Margin | Margin | Margin | Margin | Margin | Margin |

The specific preparation method is described in examples 8 to 12.

Example 8

The present example adopts the recipe of example 1 for preparation:

(1) placing a prednisolone original drug and povidone having 10 times the mass of the prednisolone original drug in ethanol having 50 times the mass of the prednisolone original drug and the povidone; stirring the mixture in a water bath at a constant temperature of 60° C. to dissolve; vaporizing the solvent; collecting a solid; and sieving the powder by an 80-mesh sieve after drying and pulverization to obtain a prednisolone-povidone solid dispersion powder;

(2) placing an antithyroid drug, a preservative, an antioxidant, and an emulsifier in distilled water and mixing evenly; and heating the mixture to 80° C. to obtain a water phase;

Example 9

The present example adopts the recipe of example 2 for preparation:

(1) weighing 8.0 g of β-cyclodextrin; adding 100 mL of water, and heating the mixture to 61° C. to prepare a saturated solution; adding a Fluocinolone original drug to boiling ethanol having 50 times the mass of the Fluocinolone original drug to dissolve, and then adding the mixture slowly in an aqueous cyclodextrin solution equimolar to the drug dropwise; stirring the mixture at constant temperature for a suitable amount of time; placing the mixture in a refrigerator at −4° C. to precipitate a solid; filtering the solid after 24 hours; washing the precipitated solid first using a small amount of ethanol for 3 times; and washing the precipitated solid using distilled water for 3 times to obtain a Fluocinolone β-cyclodextrin inclusion complex after draining and drying at 60° C.;

(2) placing an antithyroid drug, a preservative, an antioxidant, and an emulsifier in distilled water and mixing evenly; and heating the mixture to 80° C. to obtain a water phase;

(3) melting an oleaginous base and a percutaneous penetration enhancer at 80° C. and mixing the two evenly to obtain an oil phase;

(4) pouring the oil phase obtained in step (3) into the water phase obtained in step (2); heating the mixture to 80° C.; and stirring the mixture evenly;

(5) adding the Fluocinolone β-cyclodextrin inclusion complex prepared in step (1) when the temperature was reduced to 40° C.;

(6) stirring the mixture evenly and sufficiently until cooled to obtain an ointment.

Example 10

The present example adopts the recipe of example 3 for preparation:

(1) dissolving the hydrocortisone original drug in boiling ethanol 30 times the mass of the hydrocortisone original drug; placing polyethylene glycol 4000 10 times the mass of the hydrocortisone in a water bath to heat and melt; mixing the two solutions evenly; distilling off the solvent while stirring continuously; moving the mixture to an ice bath to cool and solidify; and moving the mixture into a dryer and vacuum drying to embrittle and pulverize the mixture to obtain a hydrocortisone-polyethylene glycol solid dispersion;

(2) placing an antithyroid drug, a preservative, an antioxidant, and an emulsifier in distilled water; mixing the components evenly; and heating the mixture to 80° C. to obtain a water phase;

(3) melting an oleaginous base and a percutaneous penetration enhancer a 80° C. and mixing the two evenly to obtain an oil phase;

(4) pouring the oil phase obtained in step (3) into the water phase obtained in step (2); heating the mixture to 80° C.; and stirring the mixture evenly;

(5) adding the hydrocortisone-polyethylene glycol solid dispersion prepared in step (1) when the temperature was reduced to 40° C.;

(6) stirring the mixture evenly and sufficiently until cooled to obtain an ointment.

The present example adopts the recipe of example 4 for preparation:

(1) adding hydrocortisone original drug to polyethylene glycol 400 and grinding them into a uniform suspension;

(2) placing an antithyroid drug, a preservative, an antioxidant, and an emulsifier in distilled water; mixing the components evenly; and heating the mixture to 80° C. to obtain a water phase;

(3) melting an oleaginous base and a percutaneous penetration enhancer at 80° C. and mixing the two evenly to obtain an oil phase;

(4) pouring the oil phase obtained in step (3) into the water phase obtained in step (2); heating the mixture to 80° C.; and stirring the mixture evenly;

(5) adding the hydrocortisone suspension prepared in step (1) when the temperature was reduced to 40° C.;

(6) stirring the mixture evenly and sufficiently until cooled to obtain an ointment.

Example 11

The present example adopts the recipe of example 4 for preparation:

(1) adding hydrocortisone original drug to polyethylene glycol 400 and grinding them into a uniform suspension;

(2) placing an antithyroid drug, a preservative, an antioxidant, and an emulsifier in distilled water; mixing the components evenly; and heating the mixture to 80° C. to obtain a water phase;

(3) heating an oil-soluble base and a penetration enhancer to 80° C. to melt and mixing the two evenly to obtain an oil phase;

(4) pouring the oil phase obtained in step (3) into the water phase obtained in step (2); heating the mixture to 80° C.; and stirring the mixture evenly;

(5) adding the hydrocortisone suspension prepared in step (1) when the temperature was reduced to 40° C.;

(6) stirring the mixture evenly and sufficiently until cooled to obtain an ointment.

Example 12

The present example adopts the recipe of example 5 for preparation:

(1) dissolving equimolar amounts of mometasone and soybean phospholipids in a certain amount of acetone; stirring the mixture until dissolved to a clear and transparent state; vaporizing the mixture under reduced pressure at 37° C. until dry; vacuum drying the resulting substance overnight and taking the substance the next day; and sieving the substance by a 100-mesh sieve to obtain a mometasone-soybean phospholipid complex;

(2) placing an antithyroid drug, a preservative, an antioxidant, and an emulsifier in distilled water; mixing the components evenly; and heating the mixture to 80° C. to obtain a water phase;

(3) melting an oleaginous base and a percutaneous penetration enhancer at 80° C.; and mixing the two evenly to obtain an oil phase;

(4) pouring the oil phase obtained in step (3) into the water phase obtained in step (2); heating the mixture to 80° C.; and stirring the mixture evenly;

(5) adding the mometasone-soybean phospholipid complex prepared in step (1) when the temperature was reduced to 40° C.;

(6) stirring the mixture evenly and sufficiently until cooled to obtain an ointment.

Example 13

The present example includes following typical cases of clinical treatment.

(1) The patient of this case is xxx, female, 24-years-old. Suffering from hyperthyroidism for 6 years, this patient orally took propylthiouracil and methimazole successively, but treatment was discontinued due to severe drug-induced liver damage. Hyperthyroidism was treated by applying the agent of the patent (ZL200510070954.0), and after 3 days, tightening and burning sensation started to occur on the application site on the neck and gradually became more severe until day 7 when the patient discontinued the drug on her own due to significant stinging and itching sensation and came to the clinic seeking other drug treatments. Physical examinations found that significant shrinking, scaling, and scattered papules occurred on the local skin. After discontinuing for 10 days, the skin damage improved, but symptoms of hyperthyroidism got significantly worse. Treatment was then performed using the agent of the invention (example 8). After treatment, the skin became normal; on day 28, symptoms of hyperthyroidism disappeared, and thyroid function and liver function returned to normal. Drug use was continued for 1 year, and local discomfort, skin lesions and other systemic adverse reactions were not observed, and thyroid function was stable.

(2) The patient of this case is xx, female, 30-years-old. Two months ago, the patient orally took methimazole and propylthiouracil successively for hyperthyroidism, but treatment is discontinued due to severe neutropenia. Hyperthyroidism got significantly worse after discontinuing from the drugs, and the patient was treated with the agent of the patent (ZL200510070954.0). On day 14, symptoms of hyperthyroidism significantly improved, thyroid function was significantly reduced, and granulocytes became normal. On the next day, the application site on the neck suddenly became unbearably itchy and became red and swollen. The dermatologist made the diagnosis of "contact dermatitis" and ordered the patient to discontinue using the agent of the patent (ZL200510070954.0) and provided anti-allergy treatment. After seven days, the skin lesions disappeared, but hyperthyroidism got worse. The patient requested to continue treatment using the new agent of the invention (example 9). After 28 days of treatment, thyroid function returned to normal, symptoms of hyperthyroidism disappeared, and granulocytes became normal. After continuing the drug for 8 months, no adverse reaction occurred on the application site on the neck and the rest of the body, and thyroid function was under control.

(3) The patient of this case is xxx, male, 36-years-old. The patient orally took methimazole and propylthiouracil successively for hyperthyroidism, and resulting in acute urticaria, discontinued drug use and came to the clinic for treatment. After 1 month of application of the agent of the patent (ZL200510070954.0), hyperthyroidism was under control, but a plurality of folliculitis occurred on the application site on the neck, and the dermatologist suggested the patient to discontinue the drug, and provided local treatment, and the folliculitis gradually disappeared. Hyperthyroidism returned after discontinuing the drug, and the patient agreed to continue treatment using the new agent of the invention (example 10). After 10 months of treatment, skin conditions at the application site on the neck were normal, thyroid function was normal and stable, and no allergic reaction and other side effects were observed.

Example 14

To verify the clinical treatment effects and adverse reactions of the invention (new agent of example 11), contrast observation of the clinical treatment was made with the new agent and the agent of patent (ZL200510070954.0) (original agent hereinafter). The test method was randomized, single-blind, and parallel controlled. Test subjects were divided into an experimental group using the new agent and a control group using the original agent. Treatment and observation time was 6 weeks.

The inclusion criteria were as follows: volunteers aged 18 to 65 with informed consent; Graves' disease, nodular goiter with hyperthyroidism, untreated patients with initial or recurrent hyperthyroidism, and patients treated with antithyroid drugs needed to be off of their medications for 2 weeks; free triiodothyronine ($FT_3$) and free thyroxine ($FT_4$) (thyroid function hereinafter) were higher than the upper limit of normal value. The exclusion criteria were as follows: patients with hyperthyroidism caused by Hashimoto's disease, patients with hyperthyroidism caused by subacute thyroiditis, patients treated with isotope iodine therapy, patients with ectopic goiter, pregnant women, lactating women, patients used glucocorticoids or thyroid hormones, and patients without liver dysfunction and leukopenia/granulocytopenia. Rejection criteria were as follows: those who did not cooperate in the trial, did not use the medication as instructed or discontinued using the medication without completing the treatment, those with alanine aminotransferase and/or total bilirubin exceeding double the normal upper limit during treatment, those with white blood cells less than $3.0 \times 10^9$/L (normal reference range: $4.0 \times 10^9$/L-$10.0 \times 10^9$/L) and/or granulocytes less than $1.5 \times 10^9$/L (normal reference range: $2.0 \times 10^9$/L-$7.0 \times 10^9$/L), those who had to discontinue medication due to other more severe systemic adverse reactions or severe local adverse reactions, and those who were deemed unsuitable to continue trial by researchers.

Both groups adopted ointment treatment at 0.3 g per use, 3 times a day (once in the morning, midday, and night), and the ointment was applied on the thyroid surface skin and then rubbed for several minutes so that the ointment permeated into the skin. After increased thyroid function was reduced to normal, dosage was changed to twice a day (once in the morning and night), and changed to once a day after one to two weeks for maintenance. The treatment period was followed up once every two weeks, with the sixth week being the last follow up. Treatment and observation time was 6 weeks.

Each follow-up included: (1) Inquiry: symptoms and changes of hyperthyroidism (such as increased appetite, hunger, thirst, weight loss, palpitation, heat intolerance, excessive sweating, fatigue, mood swings, dysphoria, irritability, hand trembling, insomnia, diarrhea, and susceptibility to respiratory infections) and systemic adverse reactions. (2) Physical examination: life and hyperthyroidism-related signs and changes in the skin at the application site on the neck, etc. (3) Assay: thyroid function, thyrotropin, blood routine, liver function, and blood sugar.

Statistical analysis was performed with SPSS12.0 software package, and count data was expressed as a percentage (number of cases). Between the groups, an independent sample t test or two independent sample non-parametric tests were performed. A difference of $P<0.05$ was statistically significant.

The efficacy evaluation criteria adopted "New drug (Western medicine) clinical research guidelines, endocrine system drugs clinical research guidelines: antithyroid drugs, short-term effects" issued by the Ministry of Health of the People's Republic of China, and were as follows: (1) total control: symptoms and signs were under control, and $T_3$ and $T_4$ were normal under laboratory tests; (2) partial control: symptoms disappeared, signs were still present, and $T_3$ and $T_4$ were reduced; and (3) no effect: symptoms and signs were not improved, and $T_3$ and $T_4$ were still not significantly reduced.

257 cases were accepted and randomly divided into 128 cases in the experimental group and 129 cases in the control group. No significant difference in the baseline (including age, sex, and thyroid function) was observed between the two groups (all $P>0.05$). During treatment, 6 cases were removed, in detail, 2 cases of them were removed from the experimental group due to loss, and 4 cases of them were removed from the control group due to loss (2 cases) and discontinued drug treatment from local adverse reaction (2 cases). 251 cases were completed for the test, wherein 126 cases in the experimental group and 125 cases in the control group were included in clinical efficacy statistics. 126 cases in the experimental group and 127 cases in the control group are included in adverse reaction statistics.

The results for both groups are shown in Tables 2 and 3.

TABLE 2

Comparison of clinical efficacy between experimental group and control group

| Number of cases of total control (cumulative) | Experimental group (126 cases) | Control group (125 cases) |
|---|---|---|
| at 2 weeks | 23% (20)* | 12% (10) |
| at 4 weeks | 58% (50)* | 32% (27) |
| at 6 weeks | 90% (77) | 82% (70) |

Note:
compared to control group,
*$P < 0.05$

TABLE 3

Comparison of adverse reactions between experimental group and control group

| Observation indicator | Experimental group (126 cases) | Control group (127 cases) |
|---|---|---|
| 1. Systemic adverse reaction | | |
| Incidence of leukopenia/granulocytopenia (%) | 0 | 0 |
| Incidence of drug-induced liver damage (%) | 0 | 0 |
| Incidence of drug-induced rash (%) | 0 | 0 |
| Incidence of Cushing's syndrome (%) | 0 | 0 |
| Incidence of increased blood pressure (%) | 0 | 0 |
| Incidence of increased blood sugar (%) | 0 | 0 |
| 2. Local skin adverse reaction | | |
| Incidence of skin symptoms (number of cases) | 14.3% (18)* | 24.4% (31) |
| Incidence of total skin lesion (number of cases) | 8.7% (11)* | 17.3% (22) |
| Incidence of skin irritation or allergic manifestation (number of cases) | 2.4% (3)* | 7.9% (10) |
| Incidence of skin infection (number of cases) | 0.8% (1)* | 5.5% (7) |
| Incidence of abnormal sweat secretion (number of cases) | 0% (0)* | 3.2% (4) |
| Discontinuation rate % due to local skin side effect (number of cases) | 0% (0)* | 3.9% (5) |
| Permanent discontinuing rate % due to local skin side effect (number of cases) | 0% (0) | 1.6% (2) |

Note:
compared to control group,
*$P < 0.05$

Moreover, in the 2 cases of patients who indefinitely discontinued drug use due to more severe local adverse reactions in the control group, 1 patient used the new agent without significant local side effects, and continued drug use.

Statistical analysis showed that, the total control rate of hyperthyroidism was higher in the experimental group than in the control group in the 2nd, 4th, and 6th weeks, wherein significant difference existed between the 2nd and 4th weeks, indicating the short-term effects of the new agent were significantly better those of the original agent. Neither agent resulted in significant systemic adverse reaction. In terms of local skin adverse reactions, skin symptoms, skin lesions, skin irritation or allergy, skin infections, abnormal secretion of sweat, and the discontinuation rate and permanent discontinuation rate of the drug due to local skin side effects were all lower than those of the control group, and other than the permanent discontinuation rate of the drug, the other 6 items were all significantly different, indicating the local skin adverse reactions of the new agent were significantly less than those of the original agent.

Clinical trials showed that, comparing with the original agent, the new agent significantly increases treatment effects and reduces local adverse reactions, and therefore the new agent was safer, more effective, and more compliant.

What is claimed is:

1. A preparation method for an antithyroid ointment for external application, comprising the steps of:
   (1) mixing glucocorticoids and a drug carrier material so as to evenly disperse the glucocorticoids on the drug carrier material to obtain a glucocorticoid component;
   (2) placing and evenly mixing an antithyroid drug, a water-soluble base, a preservative, an antioxidant, and an emulsifier in distilled water, and then heating to 80° C. and evenly mixing again to obtain a water phase;
   (3) melting an oleaginous base and a percutaneous penetration enhancer at 80° C., and evenly mixing to obtain an oil phase;
   (4) maintaining at 80° C. and pouring the oil phase obtained in step (3) into the water phase obtained in step (2) and evenly stirring, and adding the glucocorticoid component prepared in step (1) when the temperature drops to 40° C. to obtain a mixture; and
   (5) evenly and sufficiently stirring the mixture obtained in step (4) again until cooled to obtain an ointment,
   wherein in the ointment, a mass percentage of the glucocorticoids is 0.01% to 10%, a mass percentage of the antithyroid drug is 1% to 15%, a mass percentage of the percutaneous penetration enhancer is 0.1% to 30%, a mass percentage of the oleaginous base is 10% to 30%, and a mass percentage of the water-soluble base is 4% to 40%.

2. The preparation method of claim 1, wherein the preparation of step (1) comprises any method below:
   mixing the glucocorticoids and the drug carrier material to form a solid dispersion by a melting method, a solvent method, or a mechanical dispersion method, wherein the drug carrier material is any one of polyethylene glycol 1000 to polyethylene glycol 10000, povidone, poloxamer 188, polyoxyethylene, carboxypropyl cellulose, and carboxymethyl cellulose;
   adding the glucocorticoids to polyethylene glycol 400, and then grinding them into a uniform suspension;
   mixing the glucocorticoids and cyclodextrin and a derivative thereof to form an inclusion compound by a saturated aqueous solution method, a grinding method, an ultrasonic method, a freeze-drying method, or a spray drying method;
   mixing the glucocorticoids and a phospholipids to form a complex by an evaporation method, a vacuum drying method, a freeze-drying method, or a non-solvent precipitation method; and
   preparing the glucocorticoids in a colloidal dispersion system, wherein the colloidal dispersion system comprises any one of solid lipid nanoparticles (SLN), nanostructured lipid carriers (NLC), and polymeric micelles.

3. The preparation method of claim 1, wherein:
   the glucocorticoids comprises any one of fluocinolone and acetate thereof; triamcinolone, acetate thereof, isobutyrate thereof and succinate thereof; halcinonide; hydrocortisone, acetate thereof, butyrate thereof, butyrate propionate thereof, cipionate thereof, tertiary butyl acetate thereof, valerate thereof and aceponate thereof; dexamethasone, acetate thereof, diisopropyl fluoro phosphate ester thereof, metasulfobenzoate thereof, tert-butylacetate thereof, 2-chloro-62-fluoro ester thereof (halometasone), trioxo-undecanoate thereof, isonicotinate thereof and valerate thereof; fludrocortisone, acetate thereof and succinate thereof; triamcinolone acetonide and acetate thereof; betamethasone, acetate thereof, dipropionate thereof, acibutate thereof, valerate thereof, succinate thereof, benzoate thereof, phosphate thereof and valeroacetate thereof; beclomethasone and dipropionate thereof; clobetasol propionate; flurandrenolide; prednisone, acetate thereof and palmitate thereof; prednisolone, acetate thereof, metasulfobenzoate thereof, palmitate thereof, valerate thereof and valeroacetate thereof; diflorasone and acetate thereof; amcinonide; mometasone and furoate thereof; methylprednisolon, acetate thereof, cipionate thereof, phosphate thereof and succinate thereof; clobetasone butyrate, fluorometholone; alclometasone and dipropionate thereof; difluprednate; deprodone and propionate thereof; fludroxycortide; and desoximetasone;

the antithyroid drug comprises any one of an imidazole antithyroid drug and a thiourea antithyroid drug, wherein the imidazole antithyroid drug is methimazole or carbimazole, and the thiourea antithyroid drug is propylthiouracil or methylthiouracil;

the oleaginous base comprises any three or more of vaseline, stearic acid, glyceryl monostearate, white wax, beeswax, cetyl alcohol, stearyl alcohol, dimethyl polysiloxane, toluene polysilicon, ethylene glycol monostearate, lauric acid, and silicon oil;

the water-soluble base comprises any one or more of polyethylene glycol 200 to polyethylene glycol 600, isopropyl myristate, sodium alginate, methyl cellulose, hydroxymethyl cellulose, carboxyethyl cellulose, glycerol gelatin, and glycerin of starch;

the percutaneous penetration enhancer comprises any one or two of azone, 1-geranyl-azepan-2-one, 1-farnesyl-azepan-2-one, 2-pyrrolidone, 1-methyl-2-pyrrolidone, 5-methyl-2-pyrrolidone, 1,5-dimethyl-2-pyrrolidone, 1-ethyl-2-pyrrolidone, 2-pyrrole-5-carboxylic acid, dimethyl sulfoxide, dodecyl methyl sulfoxide, decyl methyl sulfoxide, hexamethylene lauramide, urea, and oleic acid;

the emulsifier comprises any one or two of sodium dodecyl sulfate (SDS), poloxamer 188, Tweens, Spans, Brijs, cetomacrogol 1000 (CMG), peregals, fatty alcohol polyoxyethylene ether (AEO), and alkylphenol ethoxylates (lgepon, APE);

the preservative comprises any one or more of methylparaben, ethylparaben, propylparaben, butylparaben, sorbic acid, potassium sorbate, calcium sorbate, and benzyl alcohol thymol; or the antioxidant comprises any one or more of sodium sulfite, sodium bisulfite, sodium metabisulfite, sodium thiosulfate, cysteine, thioglycerol, thioglycol, dithioglycerol, dithiooxamide, thiosorbic acid, thioglucose, isoascorbic acid, and di-tert-butyl-p-cresol.

4. The preparation method of claim 3, wherein: in the ointment, a mass percentage of the glucocorticoids is 0.02% to 1%, a mass percentage of the antithyroid drug is 3% to 10%, a mass percentage of the percutaneous penetration enhancer is 5% to 20%; a mass percentage of the oleaginous base is 12% to 25%, and a mass percentage of the water-soluble base is 10% to 30%.

5. The preparation method of claim 4, wherein: in the ointment, a mass percentage of the isopropyl myristate is 6%, a mass percentage of the stearic acid is 6%, a mass percentage of the glyceryl monostearate is 6%, and a mass percentage of the vaseline is 4%.

* * * * *